United States Patent [19]

Russell

[11] 4,411,786

[45] * Oct. 25, 1983

[54] METHOD AND APPARATUS FOR SEPARATING BLOOD FROM OTHER FLUIDS DURING OPERATIVE PROCEDURES

[76] Inventor: Richard T. Russell, 1180 Akard Dr., Reno, Nev. 89503

[*] Notice: The portion of the term of this patent subsequent to Nov. 10, 1998, has been disclaimed.

[21] Appl. No.: 308,102

[22] Filed: Oct. 5, 1981

Related U.S. Application Data

[63] Continuation-in-part of Ser. No. 73,189, Sep. 7, 1979, Pat. No. 4,299,705.

[51] Int. Cl.³ .............................................. B01D 31/00
[52] U.S. Cl. ............................... 210/321.3; 210/321.4; 422/48; 604/5
[58] Field of Search .................................... 422/47–48; 210/644, 646, 647, 188, 321.4, 321.3; 128/214 B, 214 CE, 214 F, 214 R, DIG. 3; 604/5

[56] References Cited

U.S. PATENT DOCUMENTS

| | | | |
|---|---|---|---|
| 3,212,498 | 10/1965 | McKirdy et al. | 128/DIG. 3 |
| 3,731,680 | 5/1973 | Wright et al. | 128/DIG. 3 |
| 3,844,940 | 10/1974 | Kupf et al. | 210/646 |
| 3,907,504 | 9/1975 | Hammond et al. | 422/48 |
| 3,939,069 | 2/1976 | Granger et al. | 210/646 |
| 4,102,655 | 7/1978 | Jeffery et al. | 210/188 X |
| 4,299,705 | 11/1981 | Russell | 422/47 X |

OTHER PUBLICATIONS

Galletti et al., "Heart-Lung Bypass", 5-74, 391, pp. 59, 198-208 & 253-255.

Primary Examiner—Frank A. Spear, Jr.
Attorney, Agent, or Firm—Herbert C. Schulze

[57] ABSTRACT

This invention is a method and apparatus for separating blood from other fluids added to the blood in connection with operative procedures. It is particularly exemplified by bypassing a portion of the blood during surgery through an artificial kidney apparatus or the like in conjunction with the oxygenation, simultaniously, of all blood, including that bypassed through the artificial kidney, wherein the excess fluids other than blood are removed for all practical purposes by completion of the operative procedure.

4 Claims, 7 Drawing Figures

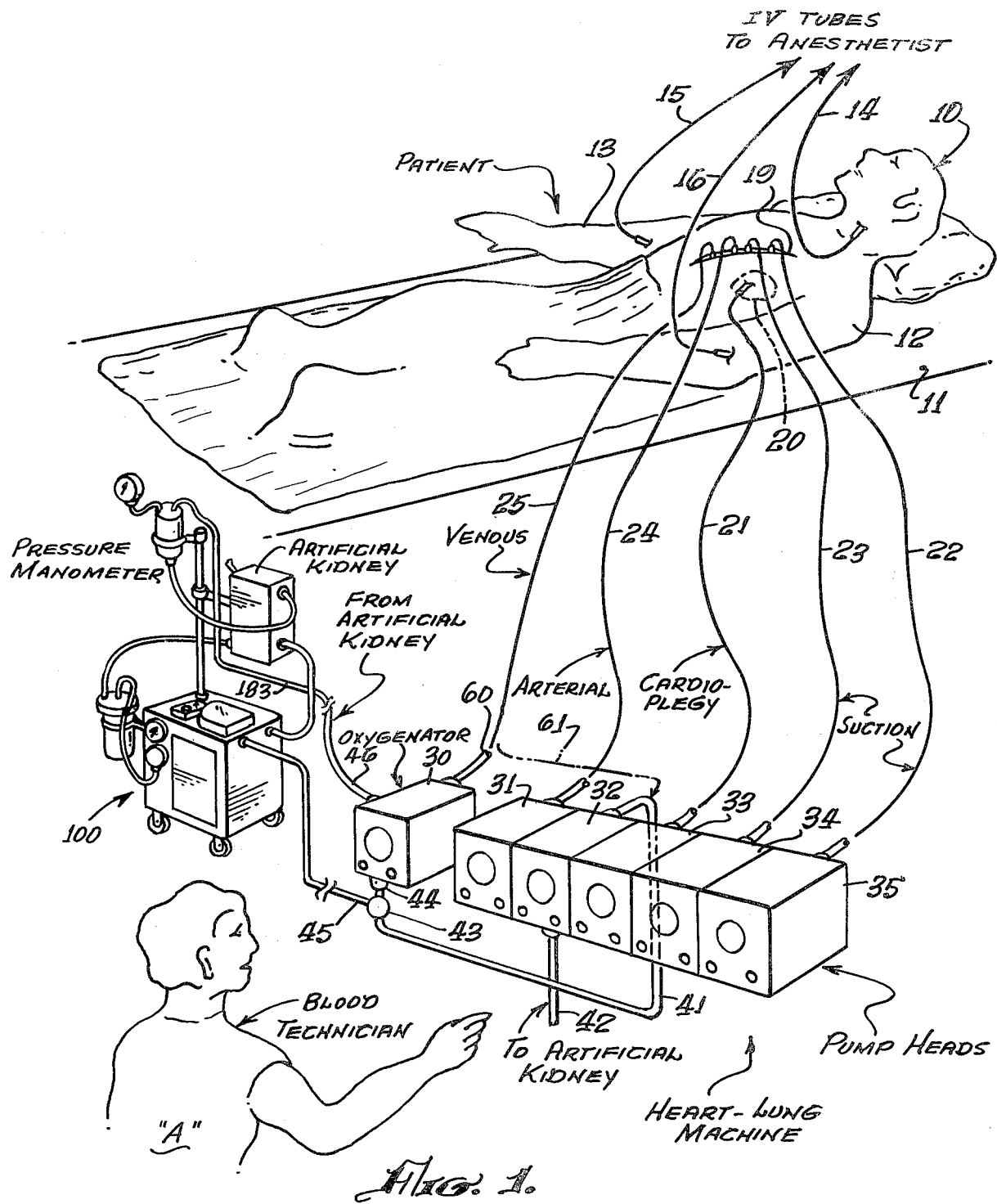

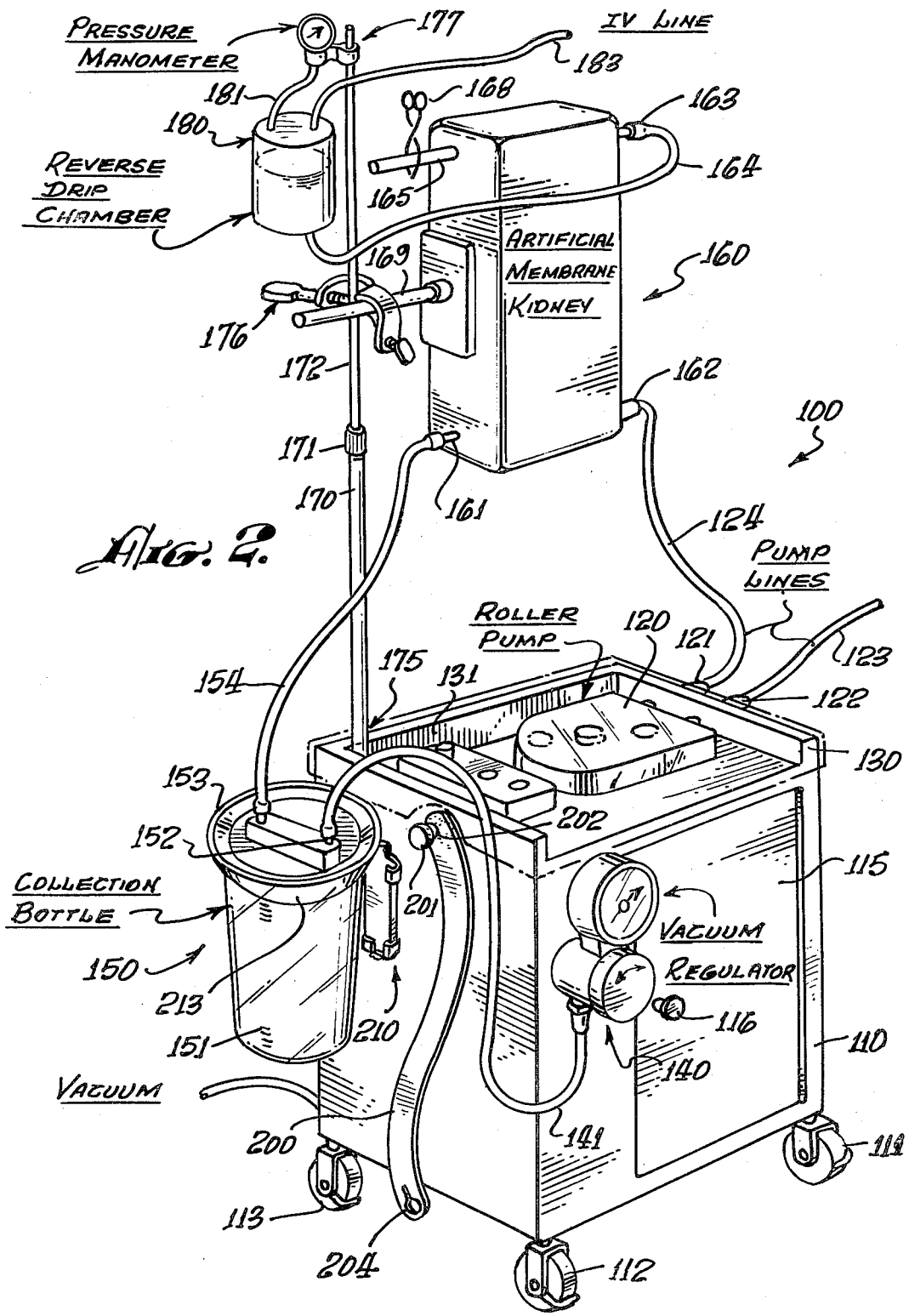

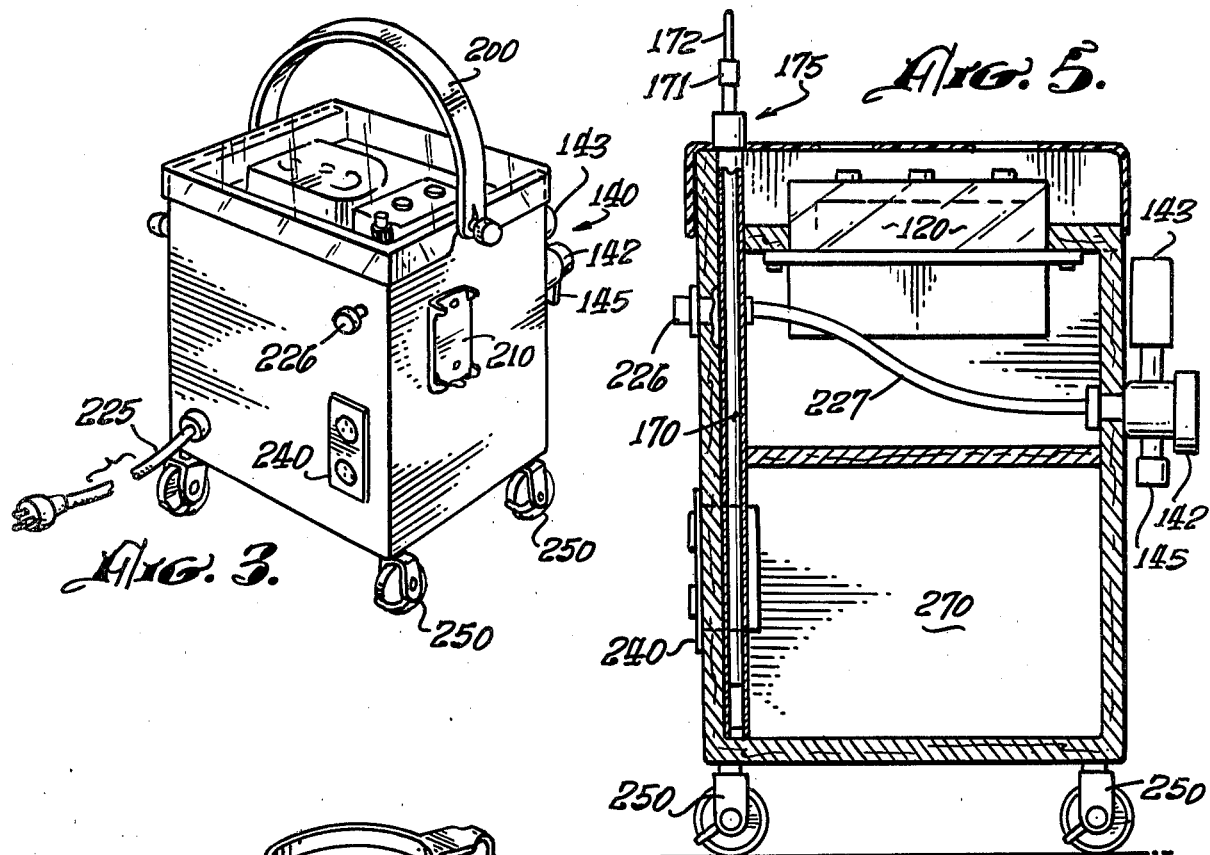
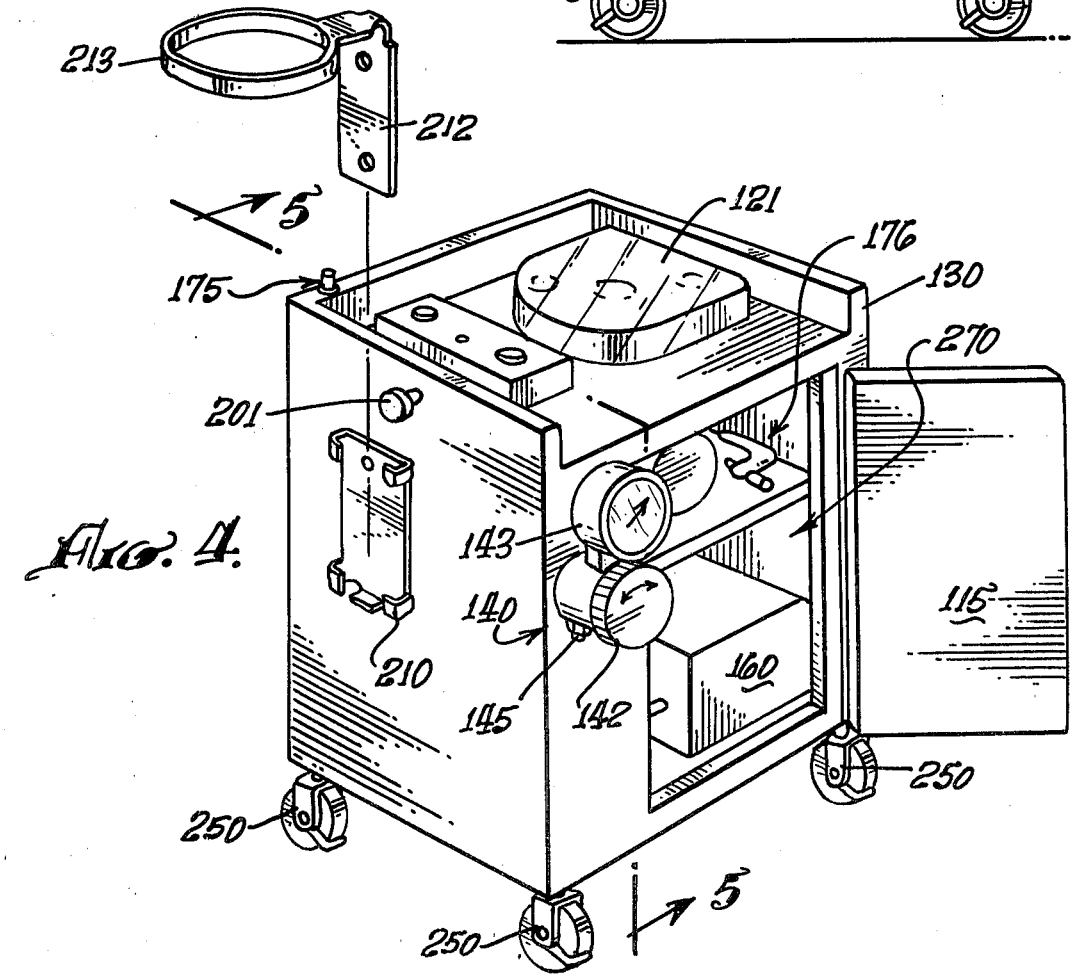

METHOD AND APPARATUS FOR SEPARATING BLOOD FROM OTHER FLUIDS DURING OPERATIVE PROCEDURES

CROSS REFERENCE TO RELATED PATENT APPLICATIONS

This is a continuation-in-part of Ser. No. 073,189, filed Sept. 7, 1979 now U.S. Pat. No. 4,299,705.

BACKGROUND OF THE INVENTION

1. Field of the Invention

This invention is in the general field of treatment of blood, and is more particularly directed to the separation of fluids from blood and is even more particularly directed to a method and apparatus for separating fluids from the natural blood during the course of, and by the conclusion of operative procedures such as open heart surgery.

2. Description of the Prior Art

There is, essentially, no prior art in this field. There is one available apparatus known as the "Cell Saver"* which is a centrifuge type device and does separate blood, but in the separation it is merely dividing the lighter and heavier constituents and does not result in a final blood product, but only the concentrated cells. The present invention is believed to be completely unique and there is no prior art relating to the separation of blood from fluids under the circumstances as described. The present invention is unique in utilizing a partial bypass of blood flowing from the oxygenator, commonly used, through an artificial kidney arrangement for recirculation through the oxygenator, by which means a technician can control the separation of fluids to the point where there has been essentially no dilution of the blood by completion of an operation.

*A Registered Trademark of Haemonetics Corporation of Braintree, Mass.

SUMMARY OF THE INVENTION

In certain major operative procedures (such as open heart surgery) during the course of the operation the blood circulation system of the patient becomes totally disassociated from the heart and lungs. An exterior pumping and oxygenating system (generally known as a "Heart-Lung Machine") is utilized to maintain blood circulation and oxygenation during the operation.

This exterior equipment must be primed with a solution prior to its use, so that there will not be a danger of air pockets entering the blood stream and in general for successful operation and maintenance of the fluid level. Sometime ago it was common to prime the system with blood from a blood bank or the like. This, however, was undesirable for a number of reasons including the danger of transmitting such conditions as Hepatitis and also, by the extremely high cost and scarcity of blood. As a result, it is most common that a saline solution or the like be utilized for the priming.

One adverse side effect of the operation wherein the heart-lung machine is used, is the great dilution of blood by reason of the fluids added, not only the prime fluid, but also other fluids added during the operation as will be known to those skilled in the art. Thus, normally at the conclusion of such surgery the patient may have a large excess of body fluid which must be removed by means of a diuretic or the like.

Also, it is generally necessary to provide excessive additional blood by transfusion.

In order to attempt to alleviate this condition, one device has been provided which is known as the "Cell Saver".* This device is primarily a centrifuge which separates the blood cells and other fluids by means of differences in density. Although this is a great improvement, it is not a complete answer since the end result is to remove certain fluids from the blood which preferably would not be removed merely because of weight differentials. It does give a concentration of cells, which is important, but it is still not the exact separation of blood as whole blood from other fluids.

This problem has plagued surgeons and others engaged in this field of activity for many years. I have studied the problem completely and observed the characteristics of blood together with the other fluids utilized in the operative procedures. I have now developed a method, and an apparatus for practicing the method, by which I am able effectively to leave the patient at the conclusion of surgery with essentially the same amount of his own blood as was available and existant at the time of commencement of the surgery. This is the first time such has been capable of achievement.

The method I use is to divert a certain amount of blood as it passes through the oxygenator into an artificial kidney apparatus which filters the fluid from the blood. The blood is then circulated from the artificial kidney back into the oxygenator to continue the process in the normal way.

In practicing my invention, the blood is being constantly circulated with the necessary fluid but by the gradual filtering and reoxygenation I am able to control the consistency such that at the conclusion of the operation the patient is essentially left with all of his own blood and without any appreciable quantity of foreign fluids.

Without the use of my method, at conclusion of an operation there can be a body weight increases as high as six or eight pounds due to the addition of fluids to the blood during the operation. Yet, by using the method and apparatus of this invention, it is now possible to complete the surgery with no appreciable increase in fluid weight in the body.

It is an object of this invention to provide a method and apparatus wherein a patient's blood may be diluted with fluids during an operation yet returned to essentially its preoperative condition upon conclusion of the operation.

Another object of this invention is to provide such a method and apparatus as heretofore set forth wherein blood cells and the blood itself are not damaged by the excessive force of centrifuge.

Another object of this invention is to provide a method and apparatus as heretofore mentioned wherein there is an economy of utilization of blood.

Another object of this invention is to provide such a method and apparatus as herein described so as to minimize the necessity of blood from an exterior source such as a blood bank.

Another object of this invention is to provide an apparatus which can be utilized in conjunction with a customary heart-lung machine to achieve the fluid separations described.

The foregoing and other objects and advantages of this invention will be understood by those skilled in the art upon reading the description of a preferred embodiment which follows in conjunction with a review of the appended drawings.

BRIEF DESCRIPTION OF THE DRAWINGS

FIG. 1 is a schematic representation of a patient during major surgery showing various circuits and connections utilized with a heart-lung machine and showing a preferred embodiment of an apparatus to practice the method of this invention in connection therewith;

FIG. 2 is an enlarged perspective of apparatus to practice the method of this invention which is illustrated in FIG. 1;

FIG. 3 is a perspective from the right rear of the same apparatus of FIG. 2 in reduced scale wherein certain of the elements have been disassembled and stowed for storage while the apparatus is not in use;

FIG. 4 is a perspective from the right front of the same of FIG. 2 in reduced scale wherein certain of the elements have been disassembled and stowed for storage while the apparatus is not in use;

FIG. 5 is a partial section in different scale on 5—5 of FIG. 4, but without showing certain of the elements which are stowed;

DESCRIPTION OF A PREFERRED EMBODIMENT

Figure 6:
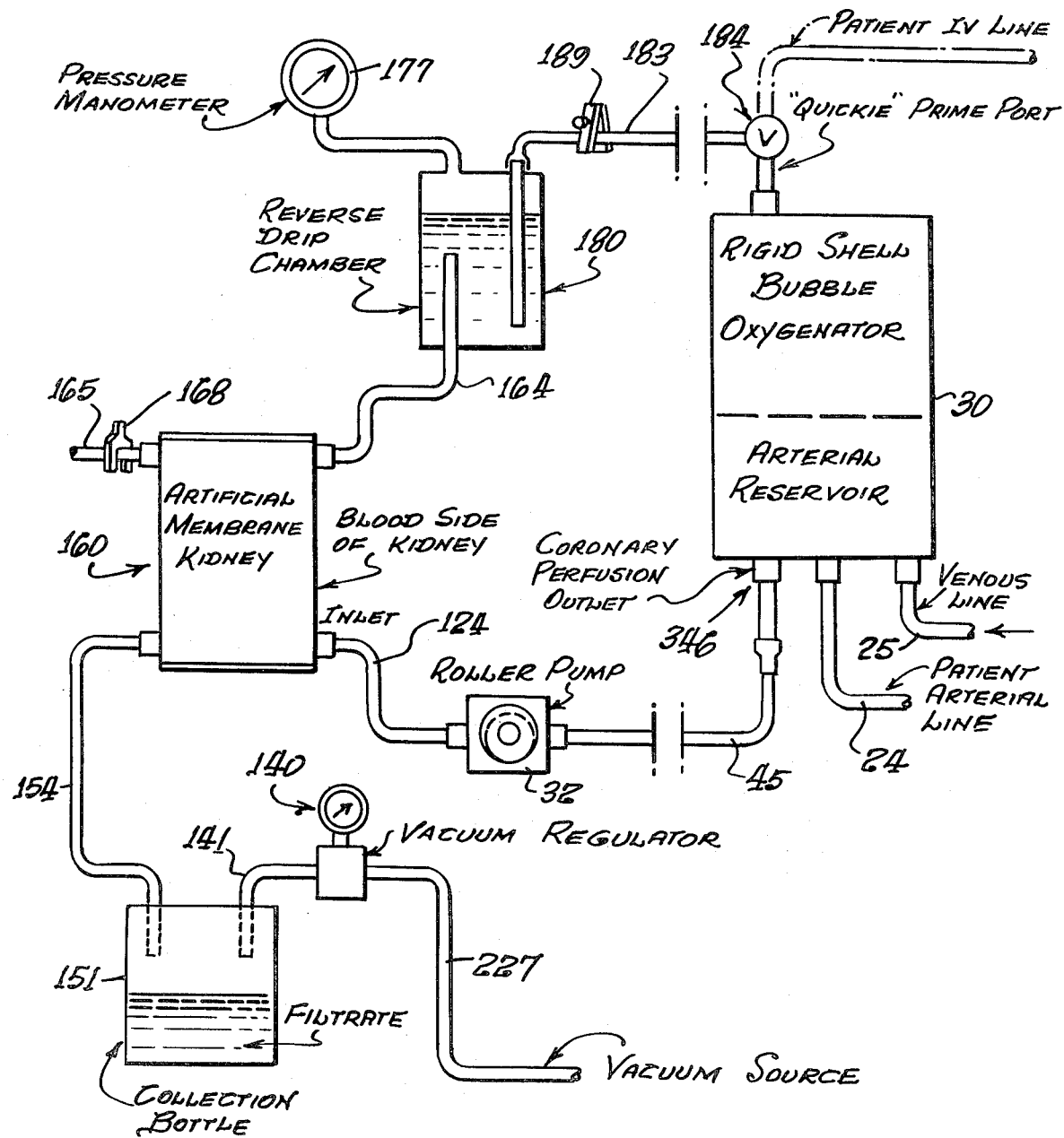
FIG. 6 is a schematic diagram of the elements utilized in the preferred apparatus for practicing the method of this invention.

Those skilled in the art will immediately recognize the familiar general situation wherein open heart surgery or the like is being performed on a patient.

A patient 10 is on an operating table, or the like, 11. A chest opening 19 is indicated, and two suction lines 22 and 23 are in place which are utilized for picking up and saving what is known in the art as "shed blood". The line 21 utilizes, generally, a needle directly into the heart for the insertion of a material known as potassium cardio-pledgy which is added to protect the heart during the surgery as is known. Line 24 will be arterial blood line, and line 25 will be the venous blood line. All of this is known to those skilled in the art. Normally, additional connections to the patient will include lines to the anesthetist and will incorporate line 15 in the arm 13, line 16 in arm 12 and line 14 from the neck. In this schetch the heart is indicated by the outline in phantom 20.

The various lines as described will run to pump heads of a heart-lung machine 30, 31, 32, 33, 34 and 35. In general, today, most heart-lung machines will have one unused pump head. In the illustration shown this would be pump head 32.

The pump heads are well known to those skilled in the art and comprise roller pumps wherein flexible tubing is placed within a channel and rollers pass over a portion of the flexible tube squeezing it down and forcing anything which is in it in the direction in which the roller travels, at the same time exerting a slight suction when the tubing returns to its normal condition after the roller passes. In this way material is pumped along the tube. It will be observed that the patient's venous line 25 connects through an element 60 to the head indicated 30, which is in fact not merely a pump head, but is an oxygenator. The workings of an oxygenator are well known to those skilled in the art, and, of course, the oxygenator supplies oxygen to the blood which then returns through connections well known to those skilled in the art, and which will be shown in more detail in other drawings, through the arterial pump head 31 and line 24.

To practice the method of this invention a line 45 and a line 46 from the oxygenator connections can be connected to two lines 123 and 183 respectively of the preferred embodiment 100 of the apparatus to practice this invention. In the alternative, however, the system can also be worked by connecting line 41 to the pump head 32 (normally unused in the heart-lung machine) with the same pump head being connected by line 42 to an artificial kidney as will be clear from a review of FIGS. 6 and 7.

In FIG. 1 the blood technician "A" is shown in position to manage the controls of the heart lung machine, oxygenator, and, in this case, the apparatus being used to practice the method of this invention.

One additional line has been shown in phantom line 61 connecting to venous line 26 at adapter 60. This line may be used for a bypass line as will be understood by the further review in more detail of actual connections and uses of the machine. The reference numerals in many cases will not be the same as the reference numerals here since these reference numerals are only for purposes of illustrating a general layout including the patient. From this point forward the description will be of specific apparatus and specific connections which will be understood by those skilled in the art.

FIG. 2 illustrates a preferred embodiment of an apparatus to practice the method of this invention.

The entire apparatus, generally 100, is carried by a cabinet 110 on four wheels 111, 112, 113 and a fourth wheel not shown in this view. There is a door 115 having a knob or the like 116 for opening, which door opens to the interior of the cabinet for service as necessary of portions within the cabinet and also for the purpose of storing elements within the cabinet when not in use. The cabinet carries a vaccuum connecting device generally 140, including a pressure regulator 142, and pressure gauge 143. The vaccuum tube 141 connects at 152 to the fluid collection arrangement generally 150 comprising a container 151 held by ring 213. At connection 153 the collection bottle is also connected by tube 154 to artificial membrane kidney 160 at 161. A handle 200 is shown hanging on one handle stud 201 by means of a slot 202. There is a like handle stud on the other side of the cabinet 110 to be connected into slot 204 for carrying as will be more specifically understood by looking at FIG. 3. The bracket 210 carries and holds the collection bottle through the ring 213 and by means of connecting element 212 as is better illustrated in FIG. 4. An upstanding edge 130-131 protects pump head 120 which is a roller pump has previously been mentioned. Connections 121 and 122 to the pump head are fitted to the pump lines 124 and 123 respectively. Line 123 will be connected to the oxygenator and the exact connection will be better understood by examining FIGS. 6 and 7. Line 124 connects to the artificial membrane kidney 160 at connection 162. The artificial membrane kidney is held in place for operation by means of clamp 176 and holding rod 169 on telescoping rod 170-171-172. This could be a solid upstanding rod, but for purposes of stowage, as will be understood, the telescoping arrangement is preferable. Any telescoping arrangement, known to those skilled in the art will satisfy this need.

The artificial membrane kidney is also connected at 163 by line 164 to a reverse drip chamber 180. The purpose of this reverse drip chamber is for maintaining desired pressure. A pressure manometer is indicated connected to the reverse drip chamber by tube 181 and is connected at 177 to the telescoping rod arrangement. Line 183 travels from the reverse drip chamber to the patient's intravenous line as indicated. The unused port of the membrane kidney at 165 should normally be clamped off by use of a clamp, or the like 168. In practice, the connections and use of the apparatus will be as is better described in connection with the schematic diagram 6 and 7 below.

FIGS. 3, 4, and 5 further illustrate features of the apparatus shown in FIG. 2. It will be noted that the wheels are provided with casters 250 having brake mechanisms on them so that the item may be locked in place and not roll unnecessarily when in use. The ring 213 which holds the collection bottle normally slides in place by its bracket 212 into bracket 210. Several of the items including the artificial kidney 160, clamp 176, and the like can be stored within the storage compartments 270 as indicated. The telescoping rod 170 collapses as indicated through mounting member 175 in a manner which will be known to those skilled in the art. Vaccuum connector 226 connects the vaccuum 227 within the cabinet to the vaccuum regulating mechanism.

A power cord 225 is provided, and, in turn, by connections known to those skilled in the art a pair of power outlets are provided on the rear of the machine at 240 for any auxiliary power requirements. The power connection within the cabinet will be customary to the pump and its controls.

FIG. 6 illustrates the preferred circuitry for practicing the method of this invention. The rigid shell bubble oxygenator 30 has connected to it in the usual manner, the venous line 25, the arterial line 24, and also has the quickie prime port 345 and the coronary profusion outlet 346. The connection through line 345 will either be to the roller pump 32 of the heart-lung machine or to the roller pump alternatively on the apparatus of FIG. 2. In either event the function will be the same. By tubing 124 from the roller pump the blood is taken from the coronary perfusion outlet to the inlet of the blood side of the kidney. The outlet of the blood side of the kidney enters the reverse drip chamber through connection 164. It will be observed that a pressure manometer 177 is connected to the reverse drip chamber and the pressure is controlled through clamp 189 applied to the exit 183 from the reverse drip chamber. The exit 183 will be connected to the quickie prime port through a three way valve or the like 184 in such manner that the blood from the reverse drip chamber may be diverted directly to the patient intravenous line or back into the rigid shell bubble oxygenator.

A customary vaccuum source will be connected through line 227 through the vaccuum regulator apparatus 140 and the vaccuum line 141 will be within the collection bottle 151 for purposes of providing proper vaccuum for proper working of the artificial membrane kidney.

The outlet from the artificial membrane kidney through tubing 154 will drain into a collection bottle 151. Artificial kidney connection 165, is clamped off by clamp 168.

Figure 7:
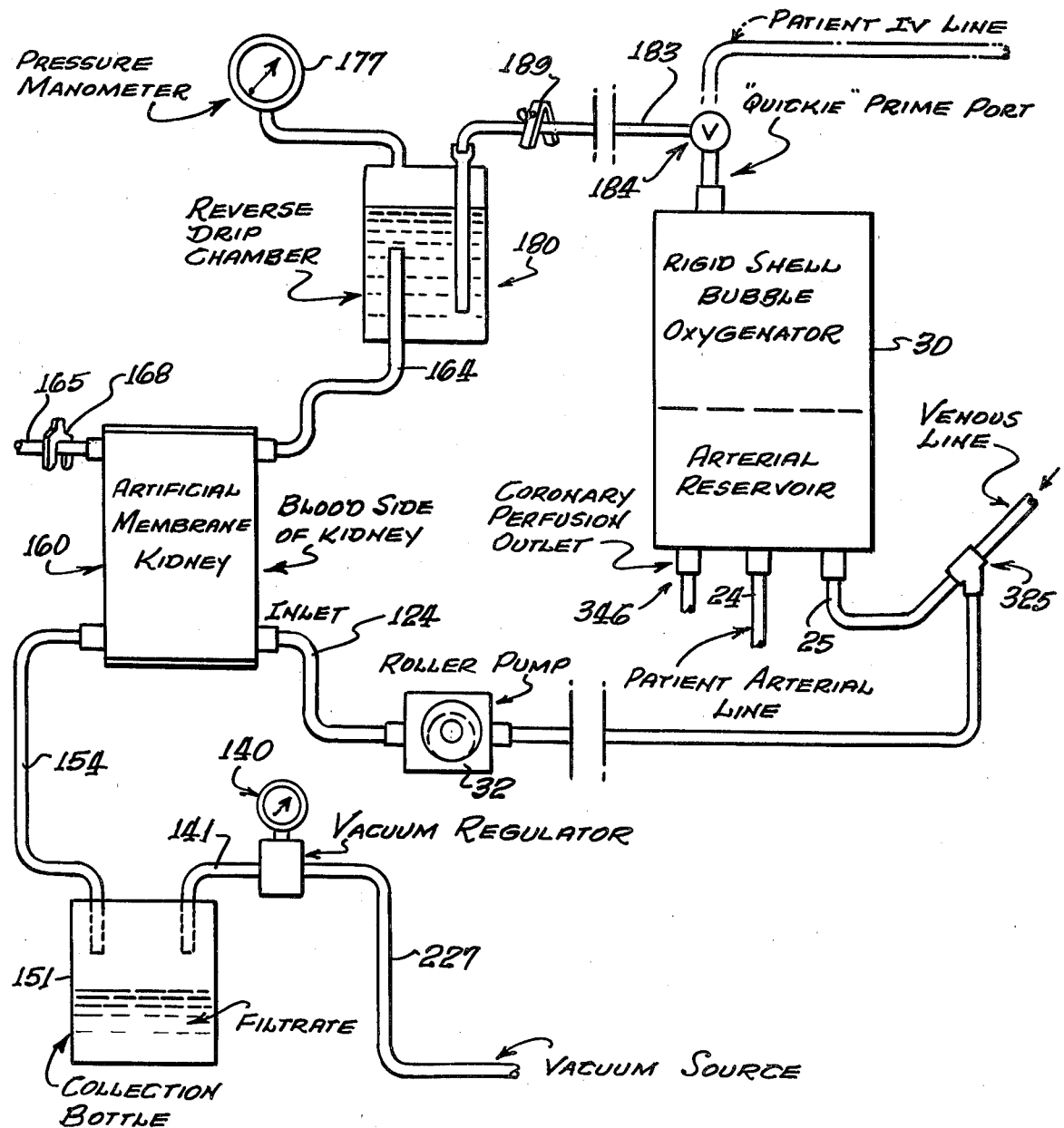
FIG. 7 is a schematic diagram of an alternate arrangement of some of the connections to the patient and heart-lung machine, which can be utilized in practicing the method of this invention.

The elements of the alternate embodiment shown in FIG. 7 are all the same as shown in FIG. 6 except that in this case the blood passing through the artificial membrane kidney is coming directly from the venous line by "Y" connection or the like 325, rather than from the coronary perfusion outlet which in this case is then not active in the system.

In operation, the techniques will be the same as are customary at the present time for commencing the operation wherein the blood technician will be operating the general blood equipment as is normal and known in the art, but will adjust the utilization of blood through the artificial kidney for purposes of achieving the proper filtration at the proper time during the surgery so that excess fluids will be gradually removed and will essentially be completely removed at the completion of the operation. The gradual filtration through the artificial membrane kidney will bring blood back from the kidney through the arrangement shown to the quickie prime port of the bubble oxygenator. The reverse drip chamber will be used to monitor the trans-membrane pressure through the appropriate guage as indicated to enable maximum artificial kidney filtration rate.

During the actual filtration in the artificial kidney, the type of dialysis is referred to as diaultrafiltration. This accomplishes the removal of fluids, electrolytes, and relatively small waste substances from the blood by convective transport through a semi-permeable membrane.

The method and equipment to be utilized for the artificial kidney will be understood by reference to the article in *Dialysis and Transplantation,* Vol. 7, No. 6, June 1978, commencing at page 567 entitled "Predialytic Isolated Ultrafiltration".

I recognize that the general method to ultrafiltration is thus known. It is, however, unique to combine this with the use of the bubble oxygenator during operative procedures to accomplish the unusually large fluid removal required to stabilize the blood as has been heretofore mentioned and described.

While the embodiments of this invention shown and described have been, and are, capable of achieving the objects and advantages desired, it must be understood that the embodiments which have shown have been for purposes of illustration only and not for purposes of limitation.

I claim:

1. The combination with a heart-lung machine used in open heart surgery of: blood removal conduit means insertable into a patient at a point adjacent the blood inlet to the heart; means to prime the heartlung machine with fluids other than blood prior to an operation; means to cause blood from a patient to flow from the patient via the blood removal conduit means into the heart lung machine to mix with the priming fluid; means to carry the blood mixed with priming fluid to the oxygenator of the heart lung machine; dual conduit means to remove the blood mixed with priming fluid from the oxygenator and deliver a first portion of the mixture to the patient via a fluid carrying conduit insertable into the patient's body and to deliver a second portion of the mixture to an artificial kidney means; means to cause the said mixture to be treated in an artificial kidney so as to separate a portion of the priming fluid from the blood; conduit means to remove the blood from which a portion of the priming fluid has been removed from the artificial kidney means and return it into the inlet of the oxygenator; and drain means to remove the priming fluid from the artificial kidney means.

2. An apparatus as set forth in claim 1 wherein a reverse drip chamber is placed between said artificial kidney means and said oxygenator.

3. The apparatus of claim 1 wherein said artificial kidney means is connected to a vacuum means.

4. The apparatus of claim 1 wherein a fluid collection chamber is connected to the artificial kidney and a vacuum source is connected to said fluid collection chamber.

* * * * *